US006562354B1

(12) United States Patent
Afriat et al.

(10) Patent No.: US 6,562,354 B1
(45) Date of Patent: *May 13, 2003

(54) COMPOSITION IN THE FORM OF A WATER-IN-OIL EMULSION HAVING AN EVOLUTIVE SHEAR RATE

(75) Inventors: Isabelle Afriat, New York, NY (US); Virginie Boulier, Lamorlaye (FR)

(73) Assignee: L'Oreal, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/611,312

(22) Filed: Jul. 6, 2000

(30) Foreign Application Priority Data

Jul. 6, 1999 (FR) .............................. 99 08712

(51) Int. Cl.$^7$ ............................. A61K 6/00; A61K 7/00; A61K 31/74; A61K 31/695; A01N 55/00
(52) U.S. Cl. ...................... 424/401; 424/78.03; 514/63; 514/937
(58) Field of Search ............... 424/401, 70.1, 424/70.12, 78.02, 78.03; 514/63, 937

(56) References Cited

U.S. PATENT DOCUMENTS

| 5,523,091 | A | * | 6/1996 | Pastour et al. ............... 424/401 |
| 5,567,426 | A | * | 10/1996 | Nadaud et al. ............... 424/401 |
| 5,665,368 | A | * | 9/1997 | Lentini et al. ............... 424/401 |
| 5,703,041 | A | * | 12/1997 | Afriat et al. ................... 514/2 |
| 5,851,539 | A | | 12/1998 | Mellul et al. ............... 424/401 |
| 5,902,569 | A | | 5/1999 | Oshima et al. ............... 424/59 |
| 5,935,559 | A | | 8/1999 | Afriat et al. |
| 5,935,588 | A | * | 8/1999 | Afriat et al. ................ 424/401 |
| 5,968,528 | A | * | 10/1999 | Deckner et al. ............ 424/401 |
| 6,149,900 | A | * | 11/2000 | Afriat et al. ............. 424/78.03 |

FOREIGN PATENT DOCUMENTS

| EP | 0 612 517 A1 | 8/1994 |
| EP | 0 670 157 A1 | 9/1995 |
| EP | 0 953 336 A1 | 11/1999 |
| EP | 0 965 331 A2 | 12/1999 |
| EP | 0 970 682 A2 | 1/2000 |
| WO | WO 93/14742 | 8/1993 |
| WO | WO 95/15812 | 6/1995 |
| WO | WO 97/14401 | 4/1997 |
| WO | WO 99/47111 | 9/1999 |

* cited by examiner

Primary Examiner—Russell Travers
Assistant Examiner—Lauren Q. Wells
(74) Attorney, Agent, or Firm—Oblon, Spivak, McClelland, Maier & Neustadt, P.C.

(57) ABSTRACT

The present provides a composition that includes, in a physiologically acceptable medium:

an aqueous phase dispersed in an oily phase with a silicone emulsifier;

wherein the aqueous phase represents at least 80% by weight relative to the total weight of the composition;

wherein the silicone emulsifier is an alkyldimethicone copolyol comprising an HLB of less than 8; and wherein a weight ratio of the oily phase to the silicone emulsifier is greater than or equal to 5. The present invention also provides a cosmetic, which includes the above-mentioned composition and methods of using the above-mentioned composition for treating, protecting, caring for, or removing make-up from the skin, lips or hair, cleansing the skin, lips or hair, and making up the skin or lips, treating, protecting, and caring for the scalp, and treating greasy skin. The composition can be used in particular in cosmetics and/or dermatology.

34 Claims, No Drawings

COMPOSITION IN THE FORM OF A WATER-IN-OIL EMULSION HAVING AN EVOLUTIVE SHEAR RATE

BACKGROUND OF THE INVENTION

1. Field of the Invention

The invention relates to a composition in the form of a water-in-oil (W/O) emulsion that includes a high content of water and a specific silicone surfactant. This composition has the appearance of a cream and is particularly suitable for use in cosmetics and/or dermatology.

2. Discussion of the Background

In cosmetics or dermatology, it is common practice to use water-in-oil (W/O) emulsion compositions which have the appearance of a cream and which contain an aqueous phase dispersed in an oily phase. These emulsions include an oily continuous phase and thus make it possible to form a lipid film at the surface of the skin which prevents transepidermal water loss and protects the skin against external attack. These emulsions are particularly suitable for protecting and nourishing the skin, and in particular for treating dry skin.

In the fields under consideration, a cream is a composition which has a certain viscosity, as opposed to liquid or semi-liquid compositions such as lotions and milks, or alternatively solid compositions.

Creams in the form of W/O emulsions, however, have the drawback of giving a fairly greasy feel when applied to the skin, since the oily phase is the external phase. Thus, these creams are generally used for dry skin, since they are too greasy to be used on greasy skin. Furthermore, W/O emulsions provide no freshness and are generally too rich in oils to be used during summer or in hot countries.

To overcome these drawbacks, it has been envisaged to prepare emulsions with a high water content. For stability reasons, however, the water content cannot be too high; alternatively, the high water content must be compensated for by adding several surfactants or gelling agents, which may undesirably reduce the comfort of the final composition and may even lead to skin irritation problems. These irritation problems may particularly arise in individuals with sensitive skin.

The need thus remains for a composition, which has the viscosity of a cream and which is in the form of a stable water-in-oil emulsion, which includes a large amount of water, which can be used in cosmetics and/or dermatology and which does not have the drawbacks of the prior art.

SUMMARY OF THE INVENTION

One object of the present invention is to provide a composition which has the viscosity of a cream and which is in the form of a stable water-in-oil emulsion.

Another object of the present invention is to provide a composition that is suitable for use in cosmetics and/or dermatology.

Another object of the present invention is to provide a composition that contains a large amount of water, but which does not have the drawbacks of the prior art.

These and other objects of the present invention may be accomplished with one embodiment of the present invention, which provides a composition that includes, in a physiologically acceptable medium:

an aqueous phase dispersed in an oily phase with a silicone emulsifier;

wherein the aqueous phase represents at least 80% by weight relative to the total weight of the composition;

wherein the silicone emulsifier is an alkyldimethicone copolyol comprising an HLB of less than 8; and wherein a weight ratio of the oily phase to the silicone emulsifier is greater than or equal to 5.

Another embodiment of the invention provides a cosmetic, which includes the above-mentioned composition.

Another embodiment of the invention provides a method selected from the group including treating, protecting, caring for, or removing make-up from the skin, lips or hair, cleansing the skin, lips or hair, and making up the skin or lips, which includes applying the above-mentioned composition to the skin, lips or hair.

Another embodiment of the invention provides a method selected from the group including treating, protecting, and caring for the scalp, which includes applying the above-mentioned composition to the scalp.

Another embodiment of the invention provides a method for treating greasy skin, which includes applying the above-mentioned composition to the skin.

DETAILED DESCRIPTION OF THE INVENTION

Various other objects, features and attendant advantages of the present invention will be more fully appreciated as the same becomes better understood from the following detailed description of the preferred embodiments of the invention.

The expression "physiologically acceptable medium" means a medium which is compatible with the skin, the lips, the nails, the scalp and/or the hair.

Despite the large amount of water, the composition of the invention is stable over time. In addition, it has a specific rheological characteristic which makes it particularly advantageous to use in the fields under consideration. Specifically, when applied to the skin, it "breaks", i.e. it suddenly becomes fluid under the effect of shear, which is probably due to a breaking phenomenon in the emulsion. Thus, the composition of the invention affords very great freshness on the skin.

Preferably, the composition obtained according to the invention has a viscosity ranging from 1.9 Pa·s (19 poises) to 20 Pa·s (200 poises). More preferably, the viscosity is from 2.0 to 18 Pa·s, more particularly preferably, the viscosity is 3.0 to 16 Pa·s. This viscosity is preferably measured using a Rheomat 180 machine, i.e. the Rheomat RM 180 machine from the company Mettler (spindle 4), at a shear rate of 200 $s^{-1}$ and at 25° C.

The composition according to the invention includes at least 80% by weight of aqueous phase relative to the total weight of the composition and preferably at least 82% of the total weight of the composition, more preferably at least 85%. The aqueous phase can be present in an amount of up to 92% of the total weight of the composition. Water preferably is present in an amount of at least 70% and more preferably at least 75% of the total weight of the composition.

Moreover, the aqueous phase of the emulsion can optionally contain one or more lower alcohols such as ethanol, in an amount preferably ranging up to 15% and better still up to 10% of the total weight of the composition, one or more polyols such as glycerol and propylene glycol in an amount ranging, for example, up to 20% and better still up to 10% of the total weight of the composition.

The emulsifier used in the composition of the invention is an alkyldimethicone copolyol or a mixture of alkyldimethicone copolyols, which is preferably the only type of emulsifier present in the composition. This emulsifier has an HLB (hydrophilic-lipophilic balance) of less than 8 and preferably less than 6. The alkyl chain of the alkyldimethicone copolyol preferably contains from 10 to 22 and more preferably from 12 to 20 carbon atoms. Alkyldimethicone copolyols which can be used, for example, are lauryldimethicone copolyol, for instance the one sold under the name Q2-5200 by the company Dow Corning, cetyldimethicone copolyol, for instance the one sold under the name Abil EM90 by the company Goldschmidt or for instance the mixture polyglyceryl-4 isostearate/cetyldimethicone copolyol/hexyl laurate sold under the name Abil WE 09 by the company Goldschmidt, oleyldimethicone copolyol, for instance the one sold under the name KF-6026 by the company Shin-Etsu, or stearyldimethicone copolyol, for instance the one sold under the name X-22-904 by the company Shin-Etsu.

The silicone emulsifier is present in an amount of active material preferably ranging from 0.5 to 4% and better still from 0.8 to 4% by weight relative to the total weight of the composition.

Even when the composition is free of any other emulsifier, it has excellent stability over time.

The oily phase/emulsifier weight ratio is greater than or equal to 5 and preferably greater than or equal to 8.

The oily phase of the composition according to the invention can contain oils and fatty substances of any kind that are well known to those skilled in the art, such as, for example, oils of plant origin (jojoba, avocado, sesame, sunflower, corn, soybean, safflower, grape seed), mineral oils (petroleum jelly, optionally hydrogenated isoparaffins), synthetic oils (isopropyl myristate, cetearyl octanoate, polyisobutylene, ethylhexyl palmitate, alkyl benzoates), volatile or non-volatile silicone oils such as polydimethylsiloxanes (PDMSs) and cyclodimethylsiloxanes or cyclomethicones, and fluoro or fluorosilicone oils, as well as mixtures of these oils.

Preferably, the oily phase of the composition of the invention includes at least one volatile silicone oil which may be present in an amount of at least 5% by weight and more preferably ranging from 5 to 25% by weight relative to the total weight of the composition. Preferred volatile silicone oils which may be mentioned, for example, are cyclic silicones (or cyclomethicones) such as pentacyclomethicone, tetracyclomethicone or hexacyclomethicone.

The oily phase can also contain other fatty constituents such as fatty alcohols, for instance stearyl alcohol, cetyl alcohol and cetearyl alcohol, and fatty acids.

The oily phase is present in the composition according to the invention in an amount preferably ranging from 7.5 to 20% and more preferably from 10 to 18% by weight relative to the total weight of the composition.

Another advantage of the composition according to the invention arises from the fact that a large amount of electrolyte can be incorporated therein without harming the stability of the composition.

Preferable electrolytes which may be mentioned, for example, are mono-, di- or trivalent metal salts, and more particularly alkaline-earth metal salts such as barium, calcium and strontium salts; alkali metal salts such as sodium and potassium salts, magnesium, beryllium, yttrium, lanthanum, cerium, praseodymium, neodymium, promethium, samarium, europium, gadolinium, terbium, dysprosium, holmium, erbium, thulium, ytterbium, lutetium, lithium, tin, zinc, manganese, cobalt, nickel, iron, copper, rubidium, aluminum, silicon and selenium salts, and mixtures thereof.

Preferable ions constituting the above salts are can be chosen, for example, from the carbonates, bicarbonates, sulphates, glycerophosphates, borates, chlorides, bromides, nitrates, acetates, hydroxides and persulphates as well as the salts of α-hydroxy acids (citrates, tartrates, lactates, malates) or of fruit acids, or alternatively the salts of amino acids (aspartate, arginate, glycocholate, fumarate). Mixtures may also be used.

Preferably, the electrolyte is a mixture of salts in particular including calcium, magnesium and sodium salts, and in particular a mixture including at least magnesium chloride, potassium chloride, sodium chloride, calcium chloride and magnesium bromide, the mixture corresponding to salts of the Dead Sea.

The content of electrolyte, when the composition contains one, preferably ranges from 0.5 to 20% and more preferably from 2.5 to 10% by weight relative to the total weight of the composition.

The composition according to the invention finds its application in a great number of treatments, in particular cosmetic treatments, for the skin, including the scalp, the hair, the nails and/or mucous membranes, in particular to care for, cleanse, make up and/or sun-protect the skin and/or mucous membranes, as well as to prepare a cream intended for treating the skin, more particularly greasy skin (provision of freshness).

Thus, a preferred embodiment of the present invention is the cosmetic or therapeutic use of the composition as defined above to treat, protect, care for, remove make-up from and/or cleanse the skin, the lips and/or the hair, and/or to make up the skin and/or lips.

Another preferred embodiment of the present invention is a treatment process for the skin, including the scalp, the hair and/or the lips, characterized in that a composition as defined above is applied to the skin, the hair and/or the lips.

Another preferred embodiment of the invention is also the use of the composition as defined above to manufacture a cream intended for treating greasy skin.

In a known manner, the composition of the invention can also contain adjuvants that are common in cosmetics and/or dermatology, such as active agents, preserving agents, antioxidants, complexing agents, solvents, fragrances, fillers, bactericides, odor absorbers, dyestuffs and lipid vesicles. The amounts of these various adjuvants are those conventionally used in the field under consideration, and, for example, from 0.01 to 20% of the total weight of the composition. Depending on their nature, these adjuvants can be introduced into the fatty phase, into the aqueous phase and/or into the lipid vesicles.

Besides the electrolytes mentioned above, active agents which may be mentioned in particular are moisturizers and, for example, protein hydrolysates and polyols such as glycerol, glycols such as polyethylene glycols, and sugar derivatives; natural extracts; procyannidol oligomers; vitamins; urea; depigmenting agents such as kojic acid and caffeic acid; beta-hydroxy acids such as salicylic acid and its derivatives; alpha-hydroxy acids such as lactic acid and glycolic acid; retinoids such as retinol and carotenoids; screening agents, and mixtures thereof.

The active agent(s) can be present, for example, in a concentration preferably ranging from 0.01 to 20%, more preferably from 0.1 to 5% and better still from 0.5 to 3%, relative to the total weight of the composition.

EXAMPLES

Having generally described this invention, a further understanding can be obtained by reference to certain specific examples which are provided herein for purposes of illustration only and are not intended to be limiting unless otherwise specified. The amounts are given as % by weight, except where otherwise mentioned.

Example 1

Cream for Greasy Skin

A. Oily Phase

| | |
|---|---|
| Cetyldimethicone copolyol | 1.15% |
| Tetracyclomethicone | 13.85% |

B. Aqueous Phase

| | |
|---|---|
| Sodium chloride | 2.5% |
| Water | 82.5% |

Procedure: the aqueous and oily phases are prepared separately and the aqueous phase is then introduced gradually into the oily phase with moderate stirring.

A white cream is obtained which has a viscosity, measured at room temperature (about 20–25° C.) with a Rheomat 180 machine, of 3.33 Pa·s (33.3 poises) at time zero. This viscosity stabilizes after 10 minutes at 3.03 Pa·s (30.3 poises).

The cream obtained is capable of moisturizing the skin and giving it a matt effect.

Example 2

Aftersun Cream

A. Oily Phase

| | |
|---|---|
| Lauryldimethicone copolyol | 1.75% |
| Pentacyclomethicone | 15.75% |

B. Aqueous Phase

| | |
|---|---|
| Sodium chloride | 2.5% |
| Water | 82.5% |

Procedure: the aqueous and oily phases are prepared separately and the aqueous phase is then introduced gradually into the oily phase with moderate stirring.

A white cream is obtained which has a viscosity, measured at room temperature (about 20–25° C.) with a Rheomat 180 machine, of 4.94 Pa·s (49.4 poises) at time zero. This viscosity stabilizes after 10 minutes at 4.42 Pa·s (44.2 poises).

The cream obtained is capable of refreshing the skin.

Example 3

Make-up Base

A. Oily Phase

| | |
|---|---|
| Oleyldimethicone copolyol | 1% |
| Pentacyclomethicone | 5.75% |
| Mixture of cetearyl octanoate and isopropyl myristate | 5.75% |

B. Aqueous Phase

| | |
|---|---|
| Sodium chloride | 2.5% |
| Water | 85% |

Procedure: the aqueous and oily phases are prepared separately and the aqueous phase is then introduced gradually into the oily phase with moderate stirring.

A white cream is obtained which has a viscosity, measured at room temperature (about 20–25° C.) with a Rheomat 180 machine, of 6.38 Pa·s (63.8 poises) at time zero. This viscosity stabilizes after 10 minutes at 4.99 Pa·s (49.9 poises).

The cream obtained is capable of moisturizing and softening the skin.

Example 4

Aftersun Cream for the Body

A. Oily Phase

| | |
|---|---|
| Stearyldimethicone copolyol | 2% |
| Pentacyclomethicone | 18% |

B. Aqueous Phase

| | |
|---|---|
| Sodium chloride | 2.5% |
| Water | 77.5% |

Procedure: the aqueous and oily phases are prepared separately and the aqueous phase is then introduced gradually into the oily phase with moderate stirring.

A white cream is obtained which has a viscosity, measured at room temperature (about 20–25° C.) with a Rheomat 180 machine, of 2.36 Pa·s (23.6 poises) at time zero. This viscosity stabilizes after 10 minutes at 2.02 Pa·s (20.2 poises).

The cream obtained is capable of refreshing the skin and giving it a satin effect.

Obviously, numerous modifications and variations of the present invention are possible in light of the above teachings. It is therefore to be understood that within the scope of the appended claims, the invention may be practiced otherwise than as specifically described herein.

This application is based on french patent application FR 9908712, filed on Jul, 6, 1999, and incorporated herein by reference in its entirety.

What is claimed is:

1. A composition in the form of a water-in-oil emulsion, comprising, in a physiologically acceptable medium:
an aqueous phase dispersed in an oily phase, a silicone emulsifier, and an electrolyte;

wherein said aqueous phase represents at least 80% by weight relative to the total weight of the composition;

wherein said silicone emulsifier is an alkyldimethicone copolyol comprising an hydrophilic-lipophilic balance (HLB) of less than 8; and wherein a weight ratio of said oily phase to said silicone emulsifier is greater than or equal to 5.

2. The composition according to claim 1, wherein said composition comprises a viscosity ranging from 1.9 Pa·s to 20 Pa·s.

3. The composition according to claim 1, further comprising at least 70% by weight water relative to the total weight of the composition.

4. The composition according to claim 1, wherein said alkyldimethicone copolyol comprises a $C_{10-22}$ alkyl chain.

5. The composition according to claim 1, wherein said alkyldimethicone copolyol is selected from the group consisting of lauryldimethicone copolyol, cetyldimethicone copolyol, oleyldimethicone copolyol, stearyldimethicone copolyol, and mixtures thereof.

6. The composition according to claim 1, wherein said silicone emulsifier is present in an amount ranging from 0.5 to 6% by weight relative to the total weight of the composition.

7. The composition according to claim 1, wherein said oily phase is present in an amount ranging from 7.5 to 20% by weight relative to the total weight of the composition.

8. The composition according to claim 1, wherein said weight ratio is greater than or equal to 8.

9. The composition according to claim 1, wherein said oily phase comprises at least one volatile silicone oil.

10. The composition according to claim 1, wherein said electrolyte is present in an amount ranging from 0.5 to 20% relative to the total weight of the composition.

11. The composition according to claim 1, further comprising at least one active agent selected from the group consisting of moisturizers, natural extracts, procyannidol oligomers, vitamins, urea, depigmenting agents, beta-hydroxy acids, alpha-hydroxy acids, retinoids, screening agents, and mixtures thereof.

12. A cosmetic, comprising the composition according to claim 1.

13. A method selected from the group consisting of treating, protecting, caring for, or removing make-up from the skin, lips or hair, cleansing the skin, lips or hair, and making up the skin or lips, comprising applying the composition according to claim 1 to the skin, lips or hair.

14. A method selected from the group consisting of treating, protecting, and caring for the scalp, comprising applying the composition according to claim 1 to the scalp.

15. A method for treating greasy skin, comprising applying the composition according to claim 1 to the skin.

16. A composition in the form of a water-in-oil emulsion consisting essentially of in a physiologically acceptable medium:

an aqueous phase dispersed in an oily phase, a silicone emulsifier, and an eletrolyte wherein said aqueous phase represents at least 80% by weight relative to the total weight of the composition;

wherein said silicone emulsifier is an alkyldimethicone copolyol comprising an hydrophilic-lipophilic balance (HLB) of less than 8; and wherein a weight ratio of said oily phase to said silicone emulsifier is greater than or equal to 5.

17. The composition according to claim 1, and containing no gelling agent.

18. The composition according to claim 1, which is free from additional emulsifiers.

19. The composition according to claim 1, having a property of suddenly becomes fluid under the effect of shear.

20. The composition according to claim 1, wherein said aqueous phase represents at least 82% by weight relative to the total weight of the composition.

21. The composition according to claim 1, wherein water is present in an amount of at least 75% by weight relative to the total weight of the composition.

22. The composition according to claim 1, wherein said composition has a viscosity ranging from 2.0 to 18 Pa·s.

23. The composition according to claim 1, wherein said composition has a viscosity ranging from 3.0 to 16 Pa·s.

24. The composition according to claim 1, wherein said aqueous phase represents at least 85% by weight relative to the total weight of the composition.

25. The composition according to claim 1, wherein said aqueous phase represents at least 92% by weight relative to the total weight of the composition.

26. The composition according to claim 16, wherein said composition has a viscosity ranging from 2.0 to 18 Pa·s.

27. The composition according to claim 16, wherein said composition has a viscosity ranging from 3.0 to 16 Pa·s.

28. The composition according to claim 16, wherein said aqueous phase represents at least 85% by weight relative to the total weight of the composition.

29. The composition according to claim 16, wherein said aqueous phase represents at least 92% by weight relative to the total weight of the composition.

30. The composition according to claim 16, wherein said electrolyte is present in an amount ranging from 0.5 to 20% relative to the total weight of the composition.

31. The composition according to claim 1, wherein said electrolyte is an alkali metal salt.

32. The composition according to claim 31, wherein said electrolyte is sodium chloride.

33. The composition according to claim 16, wherein said electrolyte is an alkali metal salt.

34. The composition according to claim 33, wherein said electrolyte is sodium chloride.

* * * * *